United States Patent [19]
Colote et al.

[11] Patent Number: 5,856,461
[45] Date of Patent: Jan. 5, 1999

[54] OLIGONUCLEOTIDES TO INHIBIT THE EXPRESSION OF ISOPRENYL PROTEIN TRANSFERASES

[75] Inventors: Soudhir Colote, Les Ulis; Eduardo Pirotzky, Paris, both of France

[73] Assignee: Societe De Conseils De Recherches Et D'Applications Scientifiques (S.C.R.A.S.), France

[21] Appl. No.: 494,301

[22] Filed: Jun. 23, 1995

[30] Foreign Application Priority Data

Jun. 29, 1994 [GB] United Kingdom .................. 9413035

[51] Int. Cl.$^6$ .................................................. C07H 21/04
[52] U.S. Cl. .......................................... 536/24.5; 536/23.1
[58] Field of Search ................... 536/23.1, 23.2, 536/24.5; 514/44

[56] References Cited

U.S. PATENT DOCUMENTS

| | | | |
|---|---|---|---|
| 4,571,421 | 2/1986 | Itakura | 536/27 |
| 5,348,853 | 9/1994 | Wang et al. | 435/6 |
| 5,420,245 | 5/1995 | Brown et al. | 530/328 |
| 5,585,479 | 12/1996 | Hoke et al. | 536/24.5 |

FOREIGN PATENT DOCUMENTS

| | | |
|---|---|---|
| 0456180 | 11/1991 | European Pat. Off. . |
| WO 90/05530 | 5/1990 | WIPO . |
| WO 92/15672 | 9/1992 | WIPO . |
| WO 93/07882 | 4/1993 | WIPO . |

OTHER PUBLICATIONS

Prendergast et al. (1993) Negative growth selection against rodent fibroblasts targeted for genetic inhibition of farnesyl transferase. Cell Growth Differ. 4:707–713, Sep. 1993.

Uhlmann et al. (1990) Antisense oligonucleotides: a new therapeutic approach. Chem. Rev. 90:543–584, Jun. 1990.

Rojanasakul (1996) Antisense oligonucleotide therapeutics: drug delivery and targeting. Adv. Drug Del. Rev. 18:115–131, 1996.

Proceedings of the National Academy of Sciences of USA, vol. 87, Washington US, pp. 3042–3046 Jackson, J. et al. 'Farnesol modification of Kirsten–ras exon 4B is essential for transformation'.

*Primary Examiner*—George C. Elliott
*Assistant Examiner*—Robert Schwartzman
*Attorney, Agent, or Firm*—Bierman, Muserlian and Lucas

[57] ABSTRACT

The invention relates to oligonucleotides and their derivatives to inhibit the expression of isoprenyl protein transferases, therapeutic compositions containing such compounds and the use of such compositions of oligonucleotides for the treatment or therapy of diseases of the human or animal body induced by an abnormal and/or uncontrolled cellular proliferation.

6 Claims, No Drawings

OLIGONUCLEOTIDES TO INHIBIT THE EXPRESSION OF ISOPRENYL PROTEIN TRANSFERASES

The invention relates to oligonucleotides and their derivatives to inhibit the expression of isoprenyl protein transferases, therapeutic compositions containing such compounds and the use of such compositions of oligonucleotides for the treatment or therapy of diseases of the human or animal body induced by an abnormal and/or uncontrolled cellular proliferation.

Any living organism, be it monocellular or multicellular, is characterized by its ability to multiply, a phenomenon requiring replication of the hereditary materials (DNA etc.) and an even distribution of the replicated DNA between the two "daughter" cells. There is a high number of very diverse molecules with mitogenic activities which act in a "cell-specific" manner. The "signal" molecules or growth factors are polypeptidic types which, in very low quantities and after interaction with target cells, can provoke a cascade of events which terminate in the replication of DNA and mitosis.

The growth factors do not act directly on the cellular cycle but by interaction and activation of a serie of transmembrane receptors located on the plasma membrane of the target cells. This mechanism triggers a chain reaction within the cell which leads to mitosis. The activated intracellular events may vary from one cell type to the next for the same receptor.

One of the first stages of linking a growth factor to its receptor is the activation of a kinase protein and phosphorylation of the proteins. One of the proteins constituting this signal transduction link is the protein ras, a 21 k-dalton protein modified by a prenylation mechanism. Prenylation is a post-translational modification which comprises the covalent linking of the isoprenyl groupings to the cysteine of the carboxy-terminal end of numerous proteins. Thus isoprenylation may be the transfer of a farnesyl grouping or a geranylgeranyl grouping to the target proteins. This modification allows certain proteins to attach themselves to the membrane action site. Thus one of the consequences of inhibiting this prenylation is to prevent the transduction of extracellular signals to the nucleus and hence cellular proliferation.

Todate, three types of enzymes which catalyze this modification have been characterised: farnesyl-protein transferase, geranyl-geranyl-protein transferase type 1 and geranyl-geranyl-protein transferase type 2. All enzymes recognize consensus sequences situated at the carboxy-terminal end of the proteins.

One of the consequences of blocking the synthesis of these enzymes is the blockage of the main signal transmission routes which lead to cellular proliferation.

Most of the classical active ingredients interact with proteins, translation product of the genetic information, and inhibit their functions. The present invention is directed to a recent therapeutic approach : the antisense strategy. The said approach is intended for the selective modulation of the expression of a gene by the selective association of a nucleotide chain (oligonucleotides) with its complementary sequence on the messenger or pre-messenger RNA or DNA, and hence inhibit the synthesis of the corresponding protein. The molecules used interact directly on the genetic information cascade.

Oligonucleotides complementary to the transcription products are termed/referred to as "antisense" oligonucleotides. Oligonucleotides having the same sequence as the transcription products are referred to as "sense" oligonucleotides. Initially, these compounds were rationally designed to inhibit the formation of a gene product by the ablation of the corresponding messenger RNA via an RNAse H mediated hydrolysis mechanism. Soon, it surfaced that the mechanism of action of these antisense oligonucleotides is not so simple. These oligonucleotides could interact with a different number of non-nucleic acid cellular targets. These oligonucleotides could interact with the gene, to form triple helice structures and inhibit the formation of the transcription products. The oligonucleotides could interact with the intron-exon junctions of the pre-messenger RNA, thus interfering with the correct splicing of the transcription product. The oligonucleotides could hybridize with the mRNA in the cytoplasm by forming a RNA-DNA duplex, which is rapidly degraded by the enzyme RNAse H or by preventing the ribosome complex from sliding over the mRNA, thus blocking the translation. The oligonucleotides, especially modified oligonucleotides, could interact with a number of cellular components such as proteins. These interactions could be sequence specific (for example : transcription factors) or could be non-sequence specific (for example: growth factors). Thus, the oligonucleotides (SEQ ID Nos. 1–36) could bring about the proliferation arrest via any one or a combination of the above mentioned mechanisms.

The invention is particularly directed to the use of antisense oligonucleotides to block the synthesis of enzymes as mentioned above. This suggests their use as antiproliferative agents in cardiovascular diseases, cancerology, dermatology, certain viral infections and any other pathological conditions which involve cellular proliferation.

In the antisense methodology, antisense oligonucleotides or antisense RNA may be used. The antisense oligonucleotide methodology is different from the antisense RNA. In the last one, a DNA segment of a gene is inserted in a vector DNA in the opposite orientation of the normal sense and, thus, during the transcription of said vector, one of the strands of its DNA is replicated in RNA. The insertion of the reverse fragment of the gene leads to the synthesis in situ of a RNA which is complementary to the normal mRNA synthesized by the cell itself. This RNA, called antisense RNA, can hybridise to the normally expressed mRNA and thus inhibit the translation of the targeted protein. Such a method has been used by Prendergast et al. (Cell Growth and differenciation 4, 707–713, September 93), to evaluate the role of the farnesyl protein transferase: the cDNA for the β sub-unit of this farnesyl protein transferase was cloned and purified; the target cells were genetically engineered to express in situ antisense RNA molecules.

The antisense RNA approach is particularly suitable as a mechanistic tool to elucidate the role of a protein in a cell, and eventually as a therapeutic agent, using sophisticated gene therapy protocols, whereas, the antisense oligonucleotides are more attractive as pharmaceuticals and are considered by the regulatory authorities as classical chemical entities. Moreover, the oligonucleotides can be easily synthesized in bulk by classical chemistry, whereas, the antisense RNA molecules are produced in a biological system and the hurdles to produce it on an industrial scale are many.

A dosage method of the farnesyl protein transferases has been investigated in EP 456180: more particularly, with said method, the activity of a potentiel inhibitor of the farnesyl protein transferases may be measured. But, in no case, such a method allows to define the structure of a new potential inhibitor of the farnesyl protein transferases, nor does this patent describe any molecule related to this present invention.

The invention provides oligonucleotides (antisense or sense) which selectively hybridize with a gene or the transcription products for sub-units of the isoprenyl protein transferases, and preferably for sub-units α and/or β of the isoprenyl protein transferases. The oligonucleotide may comprise of from 2 to 50 units and preferably of from 8 to 35 units. More preferably the oligonucleotide comprises of from 10 to 25 units.

The oligonucleotides of the invention may be synthesized by any of the known chemical oligonucleotides synthesis method. The oligonucleotides are most advantageously prepared by using any of the commercially available, automated nucleic acid synthesizers. One of the methods for the synthesis of oligonucleotides is the beta-cyanoethyl phosphoramidate method as described by S. L. Beaucage & al.(Tet. Let. 22 (1981), 1859–1862).

The invention also provides derivatives of such oligonucleotides, i.e. oligonucleotides in which the backbone has been modified on the entire length of the oligonucleotide or either or both of positions 5' and 3'. In fact oligonucleotides are sensitive to enzymes, nucleases which hydrolyse them into nucleotides; the oligonucleotides become resistant to the nucleases by modification for example of the chemical nature of the sugar itself or the phosphate-sugar internucleotide links: thus the phosphodiester chain may be replaced for example by a phosphorothioate, phosphorodithioate, methylphosphonate, phosphoramidate, phosphoethyltriester, butylamidate, piperazidate or morpholidate chain. Other types of modifications can be carried out on the entire length of the oligonucleotide or at the 5' and/or 3' extremities of the oligonucleotides to render the oligonucleotides more resistant in a biological environnement. Also, the phosphate links between the nucleotides could be replaced by amide links (peptide nucleic acids). Also, the transmembrane passage of the oligonucleotide may be promoted by rendering the latter more hydrophobic : this can be achieved, for example, by attaching hydrophobic substituents such as cholesterol or aromatic groupings or a polymer. Modified bases could be incorporated partially or on the entire length of the oligonucleotide. Also conformationally modified nucleotides (for example, oligonucleotide with α-anomer conformation) resistant to nucleases or with enhanced hybridization or intracellular uptake properties could be incorporated partially or on the entire length of the oligonucleotide. Thus, the term "derivative" comprises the nucleotide modified in one of the methods described above or any other method well known to the specialist.

The preferred oligonucleotides of the invention are the oligonucleotides of sequences SEQ ID No. 1 to SEQ ID No. 36 respectively. Their complementary sequences or sense oligonucleotides, according to the invention, may also be used.

The invention further provides oligonucleotides comprising at least a portion of one of the sequences selected of from SEQ ID No. 1 to SEQ ID No. 36.

The invention further provides therapeutic compositions comprising, as active ingredient, at least one antisense oligonucleotide according to the invention in admixture with a pharmaceutically acceptable diluent and/or carrier suitable for the selected method of administration. The composition may be administered by a topical or systemic or local treatment; it may take the form of a liquid for injection, liposome, sustained release formulation, a gel, an ointment for local application or any other acceptable form for the method of administration selected.

The invention further provides the use of a composition according to the invention in a method of treatment or therapy of the human or animal body in which the cellular proliferation is abnormal and / or uncontrolled.

Finally, the invention provides a method of treatment or therapy of the human or animal body in which the cellular proliferation is abnormal and / or uncontrolled, said method comprising administering an effective amount of an oligonucleotide according to the invention.

The following Examples illustrate the invention.

EXAMPLE 1

The effect of antisense on the proliferation of the smooth muscles of the rat

The smooth muscular cells of the aorta of male Wistar rats were isolated by enzymatic digestion (collagenase and elastase) and were cultivated in the presence of DMEM medium, 10% foetal calf serum (FCS), 2 mM glutamine, 50 U/ml penicillin and 50 µg/ml streptomycin. The smooth muscular cells were used between the 3rd and 7th passage in the 24 well plates.

After 3 days of culture, the cells were incubated in serum-free medium for 72 hours. The cells were then stimulated (or not) with 1% serum or 5 ng/ml bFGF (basic fibroblast growth factor) and treated simultaneously with or without the products of the invention at a concentration of $10^{-5}$M for 24 hours. Four hours before the end of incubation, the cells were marked with tritiated thymidine (1 µCi/ml). The incorporation is stopped by the addition of TCA 5% for 10 minutes; to the cells were then added 500 µl of 0.5N NaOH. Aliquots of 400 µl were taken and distributed in scintillation bottles containing 400 µl of 0.5N HCl and 10 ml Instagel.

The activity of oligonucleotides is determined by the measurement of the cellular proliferation expressed as a percentage. The results obtained are shown in the Table below.

|  | % of proliferation | |
| --- | --- | --- |
|  | (cells not stimulated) | (bFGF) |
| Control | 100 | 100 |
| SEQ ID No. 1 | 38 | 37 |
| SEQ ID No. 2 | 35 | 40 |
| SEQ ID No. 3 | 75 | 90 |
| SEQ ID No. 4 | 114 | 100 |
| SEQ ID No. 5 | 24 | 13 |
| SEQ ID No. 6 | 49 | 70 |
| SEQ ID No. 7 | 40 | 40 |
| SEQ ID No. 8 | 119 | 70 |
| SEQ ID No. 21 | 88 | 100 |
| SEQ ID No. 22 | 89 | 86 |
| SEQ ID NO. 23 | 58 | 59 |
| SEQ ID No. 30 | 121 | 225 |
| SEQ ID No. 31 | 103 | 111 |
| SEQ ID No. 32 | 111 | 204 |
| SEQ ID No. 33 | 9 | 2 |
| SEQ ID No. 34 | 10 | 2 |
| SEQ ID No. 35 | 13 | 2 |
| SEQ ID No. 36 | 12 | 2 |

EXAMPLE 2

Dose/Response Study - Effect of antisense on the proliferation of the smooth muscles of the rat The experimental protocol was identical to that described in Example 1. The cells were treated with compounds of the invention at concentrations of $10^{-9}$M, $10^{-8}$M, $10^{-7}$M, $10^{-6}$M and $10^{-5}$M.

|  | % of proliferation | | | | | |
|---|---|---|---|---|---|---|
| Concentration | 0 | $10^{-9}$ M | $10^{-8}$ M | $10^{-7}$ M | $10^{-6}$ M | $10^{-5}$ M |
| SEQ ID No. 1 | 100 | 99 | 108 | 107 | 64 | 25 |
| SEQ ID No. 2 | 100 | 86 | 81 | 90 | 50 | 14 |
| SEQ ID No. 5 | 100 | 95 | 80 | 100 | 66 | 20 |
| SEQ ID No. 6 | 100 | 87 | 69 | 84 | 48 | 20 |
| SEQ ID No. 7 | 100 | 102 | 98 | 96 | 59 | 28 |

EXAMPLE 3

Size effect on the in vitro biological activity of antisense oligonucleotides

The experimental protocol was identical to that described in Example 1. The cells were treated with compounds of the invention.

|  | Concentration | % of inhibition | |
|---|---|---|---|
|  | ($\mu$M) | (cells not stimulated) | (bFGF) |
| Control | — | 0 | 0 |
| SEQ ID No. 5 | 10 | 76 | 87 |
| SEQ ID No. 30 | 10 | −21 | −125 |
| SEQ ID No. 31 | 10 | −3 | −11 |
| SEQ ID No. 32 | 10 | −11 | −104 |
| SEQ ID No. 2 | 1 | 33 | 4 |
| SEQ ID No. 33 | 1 | 87 | 85 |
| SEQ ID No. 34 | 1 | 83 | 89 |
| SEQ ID No. 35 | 1 | 81 | 89 |
| SEQ ID No. 36 | 1 | 85 | 89 |

EXAMPLE 4

In vivo antiproliferative studies of antisense oligonucleotides on the angioplasty model (rat or rabbit)

Male normotensive wistar rats or New-Zealand rabbits were anesthetized and dissected to expose the aorta or the iliac artery. The artery was cleared of surrounding connective tissue and canulated with a French Fogarty Catheter. The balloon was air-inflated to distend the artery and passed three times up and down to produce deendothelializing injury.

The oligonucleotide solubilized in 25% pluronic gel was immediately applied to surround the exposed region of the artery. The wounds were closed and the animals were sacrificed after 21 days. The histomorphometric analysis of the deendothelialized artery sections was performed and the intimal and medial areas were measured.

The percentage of proliferation was determined as intimal/intimal+medial ratio.

TABLE 1

|  | Rabbit angioplasty model | |
|---|---|---|
|  | Concentration ($\mu$g) | % of proliferation |
| Control |  | 33.6 ± 8.8 |
| Placebo (pluronic gel F127) |  | 31.7 ± 5.9 |
| SEQ ID No. 2 + SEQ ID No. 5 | 200 + 200 | 16.5 ± 4.8 |

TABLE 2

|  | Rabbit angioplasty model | |
|---|---|---|
|  | Concentration ($\mu$g) | % of proliferation |
| Control |  | 46.71 ± 4.35 |
| Placebo (pluronic gel F127) |  | 45.20 ± 3.99 |
| SEQ ID No. 2 | 200 | 28.63 ± 4.51 |
| SEQ ID No. 2 (Sense) | 200 | 26.92 ± 3.40 |
| SEQ ID No. 5 | 200 | 34.99 ± 3.06 |
| SEQ ID No. 5 (Sense) | 200 | 38.37 ± 2.54 |

By convention, in all the description, the expression "SEQ ID (sense)" is the complementary oligonucleotide sequence of the oligonucleotide sequence SEQ ID.

EXAMPLE 5 a) In vitro effect of sense and antisense oligonucleotides for farnesyl transferase on C6 rat glioma cells Cells are seeded at densities of 5000 cells/dish and incubated with medium supplemented with 5% horse serum, 2.5% fetal calf serum. 24 h later, the medium is changed with one serum free plus lipofectin and different oligonucleotides at 5M concentration to perform transfections. After 5 h of incubation, the medium is replaced with a normal one thus containing 15% horse serum and 2.5% fetal calf serum. The incubation is then continued for 72 h at 37° C. Cell proliferation was evaluated by cell count after trypsinization of the monolayer using a Coulter Counter model ZM.

|  | Day 1 | Day 3 |
|---|---|---|
| Control | 267 000 ± 9 900 | 2 080 000 ± 28 700 |
| SEQ ID No. 5 | 138 000 ± 4 500 | 1 090 000 ± 10 400 |
| SEQ ID No. 5 (sense) | 288 500 ± 43 700 | 2 040 000 ± 25 200 |
| SEQ ID No. 2 | 220 000 ± 12 600 | 1 990 000 ± 17 500 |
| SEQ ID No. 2 (sense) | 157 300 ± 11 400 | 1 150 000 ± 57 500 | b) Time course effect of the oligonucleotide antisense for the α-subunit of farnesyl transferase Cells were treated as reported above and cell counts were made on parallel samples of control and oligonucleotides treated dishes at day 3, 7 and 14. The p value was <0.05% in all 3 days of experiment.

| Day | Control (Cell Number) | SEQ ID No. 5 (5 $\mu$M) (Cell Number) |
|---|---|---|
| 0 | 5 000 | 5 000 |
| 3 | 950 000 | 350 000 |
| 7 | 2 100 000 | 600 000 |
| 14 | 3 750 000 | 1 350 000 |

EXAMPLE 6

Antiproliferative studies on glioblastoma in rat a) Ex vivo effect of antisense oligonucleotides on C6 glioma cells tumorigenicity Cells were treated as described above. 24 h after transfection with oligonucleotides α-subunit for farnesyl transferase (5 $\mu$M), untreated and treated cells were intracerebrally inoculated in male Sprague-Dawley rats, 7–8 weeks old, weighing about 180–200 g. Animals were anesthetized by an i.p. injection of 1.5 mg/kg body weight of xilazine followed by an i.p. of 5 mg/kg weight of ketamine after 10 minutes. 1.5×10⁵ cells in 3 μl phosphate buffer saline, previously harvested by trypsinization, were stereotaxically injected into the left vasal ganglia 3 mm from the midline and a depth of 5 mm using a 10 μl Hamilton microsiringe. Previously we observed in rats that were sacrificed on successive days following tumor implantation that the mean survival rate was 24 days. The histological analysis of brains obtained from all animals reveal that tumor implantation was 100% successful. 2 h before sacrifice all rats were injected with 40 mg of BrdU. Animals were sacrificed by beheading. All brains were retrieved from all animals and fixed by immersion in ethanol 70% for 2 days at 4° C. Tumor proliferation was determined by means of biparametric DNA (BrdU) cytofluorimetric analysis of the two brain hemispheres.

|  | BrdU Labelling Index |
|---|---|
| Control | 4.7 ± 1.9 |
| SEQ ID No. 2 (5 μM) | 2.3 ± 0.7 |
| SEQ ID No. 5 (1 μM) | 2.4 ± 0.5 | b) In vivo effect of oligonucleotides on the in vivo tumorigenicity of C6 glioma cells Untreated C6 glioma cells were harvested from 48 h cell culture petri dishes and stereotaxically injected in the left hemisphere of rat brains as described above. Immediately after cell injection, an Alzet pump containing either the vehicle or the oligonucleotide sense and antisense (in sufficient quantity to deliver a 5 μM concentration of oligonucleotides/day), was placed on a dorsal pocket. Different agents were delivered at the site of cell injection by means of a tubing of 0.5 mm diameter. All statistical analysis were performed utilising the post-hoc Duncan test.

|  | BrdU Labelling Index |
|---|---|
| Control | 8.02 ± 0.24 |
| SEQ ID No. 5 (sense) | 6.82 ± 0.26 |
| SEQ ID No. 5 | 4.94 ± 0.3 |

---

We claim:

1. An antisense oligonucleotide which selectively hybridizes with a gene or a transcription product for a subunit of an isoprenyl protein transferase and which inhibits cellular proliferation, said oligonucleotide selected from the group consisting of SEQ ID NOS: 1 to 3, 5 to 7, 23 and 33 to 36.

2. The oligonucleotide according to claim 1, which has a modified backbone.

3. An oligonucleotide according to claim 2 wherein at least one nucleotide base is modified.

4. The oligonucleotide of claim 2 wherein at least one of the two extremities of the sequence is modified.

5. An oligonucleotide according to claim 3 wherein the modified nucleotide base has an α-anomer conformation.

6. The oligonucleotide of claim 4 wherein the modification is substitution of an hydrophobic or protecting group.

* * * * *

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 12 base pairs
        ( B ) TYPE: nucleotide
        ( C ) STRANDEDNESS: single
        ( D ) TOPOLOGY: linear ( i v ) ANTI-SENSE: Yes ( x i ) SEQUENCE DESCRIPTION: SEQ ID NO:1:

AGAAGCCATG AT                                    12

( 2 ) INFORMATION FOR SEQ ID NO:2:

( i ) SEQUENCE CHARACTERISTICS:
        ( A ) LENGTH: 12 base pairs
        ( B ) TYPE: nucleotide
        ( C ) STRANDEDNESS: single
        ( D ) TOPOLOGY: linear ( i v ) ANTI-SENSE: Yes ( x i ) SEQUENCE DESCRIPTION: SEQ ID NO:2:

GGACGTGACT GT                                    12

( 2 ) INFORMATION FOR SEQ ID NO:3:

( i ) SEQUENCE CHARACTERISTICS:
        ( A ) LENGTH: 12 base pairs
        ( B ) TYPE: nucleotide
        ( C ) STRANDEDNESS: single
        ( D ) TOPOLOGY: linear ( i v ) ANTI-SENSE: Yes ( x i ) SEQUENCE DESCRIPTION: SEQ ID NO:3:

AAGGAGTAGC AG 12

( 2 ) INFORMATION FOR SEQ ID NO:4:

( i ) SEQUENCE CHARACTERISTICS:
                ( A ) LENGTH: 12 base pairs
                ( B ) TYPE: nucleotide
                ( C ) STRANDEDNESS: single
                ( D ) TOPOLOGY: linear ( i v ) ANTI-SENSE: Yes ( x i ) SEQUENCE DESCRIPTION: SEQ ID NO:4:

CAGGCAGTAG CA 12

( 2 ) INFORMATION FOR SEQ ID NO:5:

( i ) SEQUENCE CHARACTERISTICS:
                ( A ) LENGTH: 12 base pairs
                ( B ) TYPE: nucleotide
                ( C ) STRANDEDNESS: single
                ( D ) TOPOLOGY: linear ( i v ) ANTI-SENSE: Yes ( x i ) SEQUENCE DESCRIPTION: SEQ ID NO:5:

CCCGTCGTCC AT 12

( 2 ) INFORMATION FOR SEQ ID NO:6:

( i ) SEQUENCE CHARACTERISTICS:
                ( A ) LENGTH: 12 base pairs
                ( B ) TYPE: nucleotide
                ( C ) STRANDEDNESS: single
                ( D ) TOPOLOGY: linear ( i v ) ANTI-SENSE: Yes ( x i ) SEQUENCE DESCRIPTION: SEQ ID NO:6:

CTGTCCCTGT AC 12

( 2 ) INFORMATION FOR SEQ ID NO:7:

( i ) SEQUENCE CHARACTERISTICS:
                ( A ) LENGTH: 12 base pairs
                ( B ) TYPE: nucleotide
                ( C ) STRANDEDNESS: single
                ( D ) TOPOLOGY: linear ( i v ) ANTI-SENSE: Yes ( x i ) SEQUENCE DESCRIPTION: SEQ ID NO:7:

ACTTCTCTCT CC 12

( 2 ) INFORMATION FOR SEQ ID NO:8:

( i ) SEQUENCE CHARACTERISTICS:
                ( A ) LENGTH: 12 base pairs
                ( B ) TYPE: nucleotide
                ( C ) STRANDEDNESS: single
                ( D ) TOPOLOGY: linear ( i v ) ANTI-SENSE: Yes ( x i ) SEQUENCE DESCRIPTION: SEQ ID NO:8:

ACTTGGTCCT AA                                                      12

( 2 ) INFORMATION FOR SEQ ID NO:9:

( i ) SEQUENCE CHARACTERISTICS:
        ( A ) LENGTH: 12 base pairs
        ( B ) TYPE: nucleotide
        ( C ) STRANDEDNESS: single
        ( D ) TOPOLOGY: linear ( i v ) ANTI-SENSE: Yes ( x i ) SEQUENCE DESCRIPTION: SEQ ID NO:9:

GCCATCATTC TG                                                      12

( 2 ) INFORMATION FOR SEQ ID NO:10:

( i ) SEQUENCE CHARACTERISTICS:
        ( A ) LENGTH: 12 base pairs
        ( B ) TYPE: nucleotide
        ( C ) STRANDEDNESS: single
        ( D ) TOPOLOGY: linear ( i v ) ANTI-SENSE: Yes ( x i ) SEQUENCE DESCRIPTION: SEQ ID NO:10:

GATCTGGACC AC                                                      12

( 2 ) INFORMATION FOR SEQ ID NO:11:

( i ) SEQUENCE CHARACTERISTICS:
        ( A ) LENGTH: 12 base pairs
        ( B ) TYPE: nucleotide
        ( C ) STRANDEDNESS: single
        ( D ) TOPOLOGY: linear ( i v ) ANTI-SENSE: Yes ( x i ) SEQUENCE DESCRIPTION: SEQ ID NO:11:

CTCAATAGCA TC                                                      12

( 2 ) INFORMATION FOR SEQ ID NO:12:

( i ) SEQUENCE CHARACTERISTICS:
        ( A ) LENGTH: 12 base pairs
        ( B ) TYPE: nucleotide
        ( C ) STRANDEDNESS: single
        ( D ) TOPOLOGY: linear ( i v ) ANTI-SENSE: Yes ( x i ) SEQUENCE DESCRIPTION: SEQ ID NO:12:

GTTTTTGGGC TG                                                      12

( 2 ) INFORMATION FOR SEQ ID NO:13:

( i ) SEQUENCE CHARACTERISTICS:
        ( A ) LENGTH: 12 base pairs
        ( B ) TYPE: nucleotide
        ( C ) STRANDEDNESS: single
        ( D ) TOPOLOGY: linear ( i v ) ANTI-SENSE: Yes ( x i ) SEQUENCE DESCRIPTION: SEQ ID NO:13:

TCTCACATCC TC                                                      12

( 2 ) INFORMATION FOR SEQ ID NO:14:

( i ) SEQUENCE CHARACTERISTICS:
   ( A ) LENGTH: 12 base pairs
   ( B ) TYPE: nucleotide
   ( C ) STRANDEDNESS: single
   ( D ) TOPOLOGY: linear ( i v ) ANTI-SENSE: Yes ( x i ) SEQUENCE DESCRIPTION: SEQ ID NO:14:

TTGTAAGAAC TG											12

( 2 ) INFORMATION FOR SEQ ID NO:15:

( i ) SEQUENCE CHARACTERISTICS:
      ( A ) LENGTH: 12 base pairs
      ( B ) TYPE: nucleotide
      ( C ) STRANDEDNESS: single
      ( D ) TOPOLOGY: linear ( i v ) ANTI-SENSE: Yes ( x i ) SEQUENCE DESCRIPTION: SEQ ID NO:15:

GAAGTGCTTC TC											12

( 2 ) INFORMATION FOR SEQ ID NO:16:

( i ) SEQUENCE CHARACTERISTICS:
      ( A ) LENGTH: 12 base pairs
      ( B ) TYPE: nucleotide
      ( C ) STRANDEDNESS: single
      ( D ) TOPOLOGY: linear ( i v ) ANTI-SENSE: Yes ( x i ) SEQUENCE DESCRIPTION: SEQ ID NO:16:

GCCTCTTTTC AG											12

( 2 ) INFORMATION FOR SEQ ID NO:17:

( i ) SEQUENCE CHARACTERISTICS:
      ( A ) LENGTH: 12 base pairs
      ( B ) TYPE: nucleotide
      ( C ) STRANDEDNESS: single
      ( D ) TOPOLOGY: linear ( i v ) ANTI-SENSE: Yes ( x i ) SEQUENCE DESCRIPTION: SEQ ID NO:17:

GGCATCTGTC AG											12

( 2 ) INFORMATION FOR SEQ ID NO:18:

( i ) SEQUENCE CHARACTERISTICS:
      ( A ) LENGTH: 12 base pairs
      ( B ) TYPE: nucleotide
      ( C ) STRANDEDNESS: single
      ( D ) TOPOLOGY: linear ( i v ) ANTI-SENSE: Yes ( x i ) SEQUENCE DESCRIPTION: SEQ ID NO:18:

CGGCTGGCAT CC											12

( 2 ) INFORMATION FOR SEQ ID NO:19:

( i ) SEQUENCE CHARACTERISTICS:
      ( A ) LENGTH: 12 base pairs
      ( B ) TYPE: nucleotide
      ( C ) STRANDEDNESS: single
      ( D ) TOPOLOGY: linear ( i v ) ANTI-SENSE: Yes ( x i ) SEQUENCE DESCRIPTION: SEQ ID NO:19:

GAACTGACAC AC                                                                                           12

( 2 ) INFORMATION FOR SEQ ID NO:20:

( i ) SEQUENCE CHARACTERISTICS:
        ( A ) LENGTH: 12 base pairs
        ( B ) TYPE: nucleotide
        ( C ) STRANDEDNESS: single
        ( D ) TOPOLOGY: linear ( i v ) ANTI-SENSE: Yes ( x i ) SEQUENCE DESCRIPTION: SEQ ID NO:20:

ACGATCACAT CA                                                                                           12

( 2 ) INFORMATION FOR SEQ ID NO:21:

( i ) SEQUENCE CHARACTERISTICS:
        ( A ) LENGTH: 12 base pairs
        ( B ) TYPE: nucleotide
        ( C ) STRANDEDNESS: single
        ( D ) TOPOLOGY: linear ( i v ) ANTI-SENSE: Yes ( x i ) SEQUENCE DESCRIPTION: SEQ ID NO:21:

ATCAACATGC AG                                                                                           12

( 2 ) INFORMATION FOR SEQ ID NO:22:

( i ) SEQUENCE CHARACTERISTICS:
        ( A ) LENGTH: 12 base pairs
        ( B ) TYPE: nucleotide
        ( C ) STRANDEDNESS: single
        ( D ) TOPOLOGY: linear ( i v ) ANTI-SENSE: Yes ( x i ) SEQUENCE DESCRIPTION: SEQ ID NO:22:

CTGCATATCG AC                                                                                           12

( 2 ) INFORMATION FOR SEQ ID NO:23:

( i ) SEQUENCE CHARACTERISTICS:
        ( A ) LENGTH: 12 base pairs
        ( B ) TYPE: nucleotide
        ( C ) STRANDEDNESS: single
        ( D ) TOPOLOGY: linear ( i v ) ANTI-SENSE: Yes ( x i ) SEQUENCE DESCRIPTION: SEQ ID NO:23:

CAGTGCACCA GC                                                                                           12

( 2 ) INFORMATION FOR SEQ ID NO:24:

( i ) SEQUENCE CHARACTERISTICS:
        ( A ) LENGTH: 12 base pairs
        ( B ) TYPE: nucleotide
        ( C ) STRANDEDNESS: single
        ( D ) TOPOLOGY: linear ( i v ) ANTI-SENSE: Yes ( x i ) SEQUENCE DESCRIPTION: SEQ ID NO:24:

CTGCAGCCTC GG                                                                                        12

( 2 ) INFORMATION FOR SEQ ID NO:25:

( i ) SEQUENCE CHARACTERISTICS:
          ( A ) LENGTH: 12 base pairs
          ( B ) TYPE: nucleotide
          ( C ) STRANDEDNESS: single
          ( D ) TOPOLOGY: linear ( i v ) ANTI-SENSE: Yes ( x i ) SEQUENCE DESCRIPTION: SEQ ID NO:25:

ACTCTCTGGA CC                                                                                        12

( 2 ) INFORMATION FOR SEQ ID NO:26:

( i ) SEQUENCE CHARACTERISTICS:
          ( A ) LENGTH: 12 base pairs
          ( B ) TYPE: nucleotide
          ( C ) STRANDEDNESS: single
          ( D ) TOPOLOGY: linear ( i v ) ANTI-SENSE: Yes ( x i ) SEQUENCE DESCRIPTION: SEQ ID NO:26:

CAAGAATCCT CG                                                                                        12

( 2 ) INFORMATION FOR SEQ ID NO:27:

( i ) SEQUENCE CHARACTERISTICS:
          ( A ) LENGTH: 12 base pairs
          ( B ) TYPE: nucleotide
          ( C ) STRANDEDNESS: single
          ( D ) TOPOLOGY: linear ( i v ) ANTI-SENSE: Yes ( x i ) SEQUENCE DESCRIPTION: SEQ ID NO:27:

ACATCTGCTC TG                                                                                        12

( 2 ) INFORMATION FOR SEQ ID NO:28:

( i ) SEQUENCE CHARACTERISTICS:
          ( A ) LENGTH: 12 base pairs
          ( B ) TYPE: nucleotide
          ( C ) STRANDEDNESS: single
          ( D ) TOPOLOGY: linear ( i v ) ANTI-SENSE: Yes ( x i ) SEQUENCE DESCRIPTION: SEQ ID NO:28:

TCTGTACTCG TC                                                                                        12

( 2 ) INFORMATION FOR SEQ ID NO:29:

( i ) SEQUENCE CHARACTERISTICS:
          ( A ) LENGTH: 12 base pairs
          ( B ) TYPE: nucleotide
          ( C ) STRANDEDNESS: single
          ( D ) TOPOLOGY: linear ( i v ) ANTI-SENSE: Yes ( x i ) SEQUENCE DESCRIPTION: SEQ ID NO:29:

CTACAGTACA GC                                                                                        12

( 2 ) INFORMATION FOR SEQ ID NO:30:

(i) SEQUENCE CHARACTERISTICS:
 (A) LENGTH: 15 base pairs
 (B) TYPE: nucleotide
 (C) STRANDEDNESS: single
 (D) TOPOLOGY: linear (iv) ANTI-SENSE: Yes (xi) SEQUENCE DESCRIPTION: SEQ ID NO:30:

CCCGTCGTCC ATAGG 15

(2) INFORMATION FOR SEQ ID NO:31:

(i) SEQUENCE CHARACTERISTICS:
 (A) LENGTH: 18 base pairs
 (B) TYPE: nucleotide
 (C) STRANDEDNESS: single
 (D) TOPOLOGY: linear (iv) ANTI-SENSE: Yes (xi) SEQUENCE DESCRIPTION: SEQ ID NO:31:

CCCGTCGTCC ATAGGGGA 18

(2) INFORMATION FOR SEQ ID NO:32:

(i) SEQUENCE CHARACTERISTICS:
 (A) LENGTH: 21 base pairs
 (B) TYPE: nucleotide
 (C) STRANDEDNESS: single
 (D) TOPOLOGY: linear (iv) ANTI-SENSE: Yes (xi) SEQUENCE DESCRIPTION: SEQ ID NO:32:

CCCGTCGTCC ATAGGGGACG C 21

(2) INFORMATION FOR SEQ ID NO:33:

(i) SEQUENCE CHARACTERISTICS:
 (A) LENGTH: 15 base pairs
 (B) TYPE: nucleotide
 (C) STRANDEDNESS: single
 (D) TOPOLOGY: linear (iv) ANTI-SENSE: Yes (xi) SEQUENCE DESCRIPTION: SEQ ID NO:33:

GGACGTGACT GTTTC 15

(2) INFORMATION FOR SEQ ID NO:34:

(i) SEQUENCE CHARACTERISTICS:
 (A) LENGTH: 18 base pairs
 (B) TYPE: nucleotide
 (C) STRANDEDNESS: single
 (D) TOPOLOGY: linear (iv) ANTI-SENSE: Yes (xi) SEQUENCE DESCRIPTION: SEQ ID NO:34:

GGACGTGACT GTTTCCAC 18

(2) INFORMATION FOR SEQ ID NO:35:

(i) SEQUENCE CHARACTERISTICS:
 (A) LENGTH: 21 base pairs
 (B) TYPE: nucleotide
 (C) STRANDEDNESS: single
 (D) TOPOLOGY: linear (i v) ANTI-SENSE: Yes (x i) SEQUENCE DESCRIPTION: SEQ ID NO:35:

GGACGTGACT GTTTCCACTG A                                              21

(2) INFORMATION FOR SEQ ID NO:36:

(i) SEQUENCE CHARACTERISTICS:
        (A) LENGTH: 24 base pairs
        (B) TYPE: nucleotide
        (C) STRANDEDNESS: single
        (D) TOPOLOGY: linear (i v) ANTI-SENSE: Yes (x i) SEQUENCE DESCRIPTION: SEQ ID NO:36:

GGACGTGACT GTTTCCACTG AGTC                                           24